United States Patent [19]

Hiller et al.

[11] 4,144,568
[45] Mar. 13, 1979

[54] EXERCISE RECORDER

[76] Inventors: Alexander J. Hiller, 13045 Tompkins La., Bowie, Md. 20715; Frank M. Hardy, 15714 Dorset Rd., Laurel, Md. 20810

[21] Appl. No.: 724,263

[22] Filed: Sep. 17, 1976

[51] Int. Cl.$^2$ .................. G01L 5/02; H01H 1/00
[52] U.S. Cl. ............................. 364/410; 273/70; 273/100; 325/66; 335/196; 364/413; 364/556
[58] Field of Search ......... 235/151.3, 151.32, 92 MT; 73/379–381; 335/207, 196; 272/93, 100, 70; 364/410, 413, 415, 561; 325/66, 102

[56] References Cited

U.S. PATENT DOCUMENTS

| | | | |
|---|---|---|---|
| 3,594,669 | 7/1971 | Yamane et al. | 335/207 |
| 3,599,132 | 8/1971 | Shlesinger, Jr. | 335/207 |
| 3,733,569 | 5/1973 | Yanagisawa et al. | 335/207 |
| 3,797,010 | 3/1974 | Adler et al. | 272/70 |
| 3,846,704 | 11/1974 | Bessette | 325/66 |
| 3,895,356 | 7/1975 | Kraus | 235/151.32 |
| 3,950,719 | 4/1976 | Maxwell | 335/207 |
| 3,955,073 | 5/1976 | Carew et al. | 235/151.32 |
| 3,980,979 | 9/1976 | Prosser et al. | 335/207 |
| 3,995,492 | 12/1976 | Clynes | 73/379 |
| 4,019,163 | 4/1977 | Beavitt | 335/196 |
| 4,053,755 | 10/1977 | Sherrill | 364/561 |

FOREIGN PATENT DOCUMENTS 1278762   6/1972   United Kingdom .................. 335/207

Primary Examiner—Charles E. Atkinson
Assistant Examiner—Errol A. Krass

[57] ABSTRACT

A combined sensor-transducer with a calculator or computer is provided in which the sensor senses mechanical motions as in muscular exercising to provide a transduced pulse to the calculator or transducer to tally the number of muscular movements or by inserting a factor in the computer to read out the pulses in terms of calories or energy. An improved type of reed switch is provided for sensing mechanical motions in which a magnet is slidably supported near magnetically responsive metal lead wires, the magnetic flux with each movement of the slidable magnet bending the wires into conductive contact.

14 Claims, 11 Drawing Figures

U.S. Patent  Mar. 13, 1979  Sheet 1 of 3  4,144,568
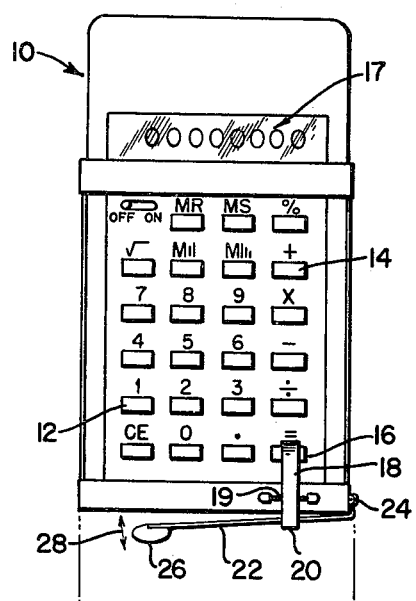
FIG.1
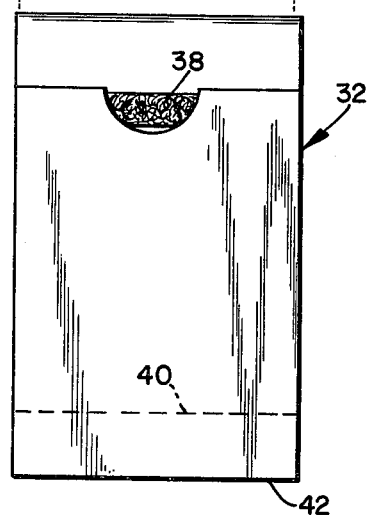
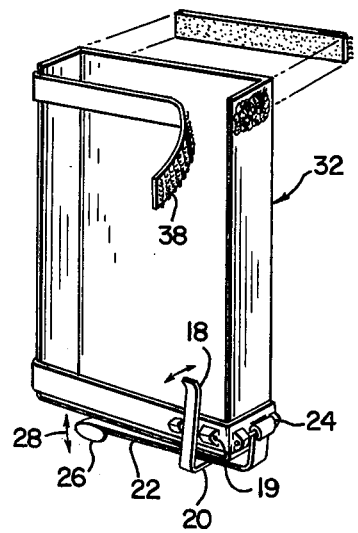
FIG.2
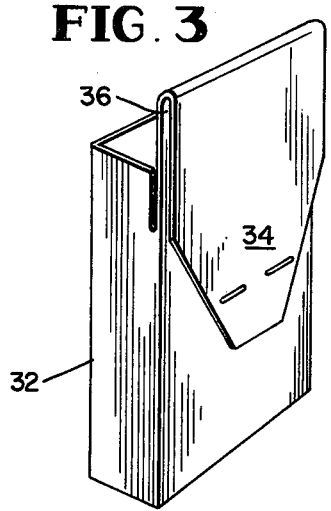
FIG.3
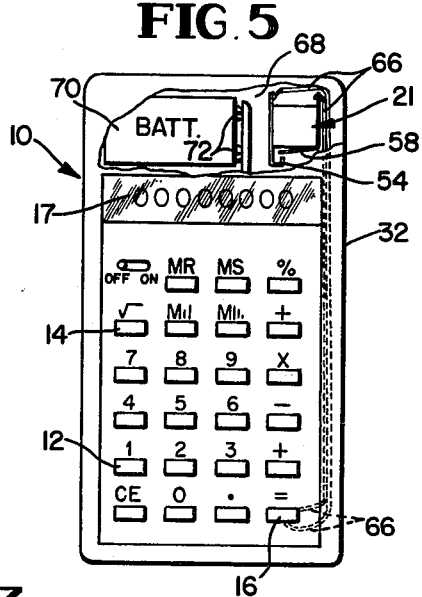
FIG.5
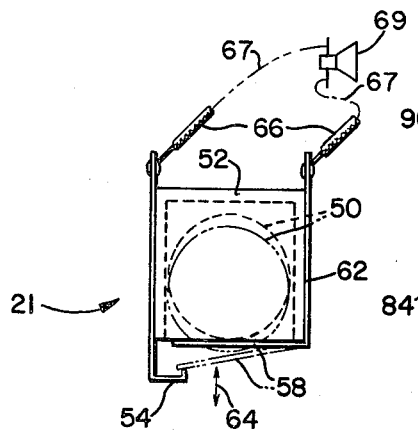
FIG.4
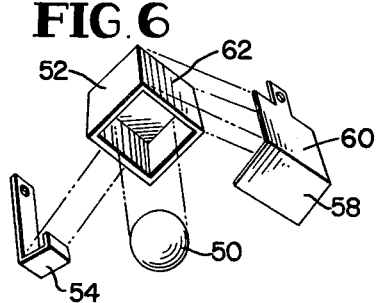
FIG.7  FIG.6

EXERCISE RECORDER

The invention relates to an exercise recording device, including, in combination, a counting means, such as a calculator or computer, and a shock or pulse sensor-transducer in which the sensor senses mechanical pulses, such as muscular movements in a body, typically as in exercising, such as walking, jogging, swimming, running or the like, transmitting said pulses to a counter, calculator or computer to indicate the muscular movements in counted or modified data form in which each muscular movement is a factor. It further relates to improved pulse transducing means responsive to such movements.

In one aspect thereof, the invention is in a combination of a calculator, or, more sophisticated, a computer and a pulse sensor in which the sensor is a transducer which signals muscular movement, typically muscular movement of a human body. The signal transmitting the pulses to the calculator or computer may be directly counted or may be a modified counting measurement to interpret such muscular pulse in terms of energy expended in the numerically counted units. The combination may also be used for counting by mechanical or an electrical pulse which operates a computer. The term computer hereinafter is used in a generic sense to include both the elementary form, a calculator, or more sophisticated, computer form. In preferred form, the pulse sensor and computer are easily portable and carried by the user for measurement of the human exercising.

The counting may be done by a small computer and the pulse sensor may be an accelerometer or shock sensor sensitive to be activated by the muscular movements present in the walking, jogging, running, or the like, measuring the exercise motion in unitary form, such as a pace or stride to which the pulse sensor is sensitive to responsively produce a measurable or countable pulse.

Thus, according to the invention each muscular movement is picked up by the sensor-transducer which signals the computer and which tallies or modifies the count of the movements to electronically measure the total exercise in selected terms, such as a Calorie count, exercising rate, distance or other output information useful to the exercising human.

The sensor or accelerometer may take any of several forms as described in detail below. It may be a mass-loaded lever attached to a pocket-sized computer operative with each exercising pulse to depress the input calculator key in each stride, pace or mechanical jerk evolved in the exercising. Alternately, it may be a free moving mass impacting by each muscular movement against a switch means to trigger an electrical pulse.

In another aspect of the invention, an improved sensor is provided comprising a reed switch mountable in a counting circuit for counting electrical pulses actuated by exercise induced movement of a freely movable magnet. Such movable magnet is confined to slide in a path which approaches sufficiently close to an arm of the magnetically responsive reed switch to close a circuit, in close proximity, and to allow the reed switch to open as the magnet moves away from the contact position thereof. The moving magnet is one of a pair of magnets mounted with opposed polarity to each other to normally repel each other, whereby the movable magnet is biased away from the stationary magnet by the magnetic repelling flux. However, as such switch assembly is mounted to move with each exercising movement, the slidable magnet will responsively slide oscillatingly, closer and more distant from the stationary magnet, thus varying the magnetic field with each muscular pulse, and responsively, to magnetically close and then open the reed switch elements. The alternate switching of the current in the reed switch passes the current to a receiving means, such as the computer, to count or modify the available data from mechanical movements of the exerciser.

In a preferred form, as stated, the computer will be pocket-sized for carrying by the exerciser. For this purpose a carrying case is provided, in another aspect of this invention, having a built-in sensor and having an arm positioned to contact an equals or repeat key of computer, whereby a normal commercial form of such portable computer need merely be inserted, i.e. "plugged in" to the carrying case, and by setting the calculator or programming the computer to a selected program and merely inserting such computer in the carrying case, the user may proceed with whatever type of exercise he selects, and the computer will display the result as a tally or as modified data such as Calories expended, varied with the exercise or with the timing as desired. Such plug-in type of portable computer and case is worn, such as by fastening to a belt, or carried in a pocket as the user exercises.

The sensor is most commonly attached to a small pocket-sized computer operated by the motion of the exerciser both to sense and tally the motions of the exercising. There is direct connection of sensor to computer to perform a simple tally of exercising pulses first sensed and then carried electrically or mechanically from the sensor to the computer in neighboring association therewith as an electrical or mechanical circuit. However, the transfer of the electrical pulses from the sensor to the computer may be over any necessary distances interconnected by wiring or by radio signaling. In that case the computer can be large and may process numerous signals broadcast by a group of exercisers to provide useful exercise data. For these purposes both the computer and sensor are modified for radio signaling therebetween, whereby the sensor and computer may be separated a significant distance. In such use, several sensors, one carried by each member of a group of exercisers even remotely distributed, such as players on a playing field, gymnasiums or the like, in which each exerciser can be connected to a computer, even a stationary computer having multiple reception of numerous signals, whereby an entire supply group or platoon of many exercisers may have their individual efforts computed to show the exercising output of each in such data measurement terms as will appear most useful to the users.

The invention is further described in relation to the drawings, wherein:

FIG. 1 shows a computer in simplest form combined with a massloaded lever sensor associated with a belt mountable container;

FIG. 2 shows a perspective view of a "plug-in" carrier useful with the device of FIG. 1 with the parts broken away to show internal construction;

FIG. 3 shows the container for fastening to the belt of the exerciser;

FIG. 4 shows the transducer as an inertial mass mountable in a box to depress a lever connected to an output key for transferance of transduced pulses to a calculator for each muscular movement of the exerciser;

FIG. 5 shows the face of a pocket computer with the upper portion broken open to show housing of a pulsing transducer device therein;

FIG. 6 shows detailed construction of the movable inertial mass operated switch of FIG. 4;

FIG. 7 shows a reed switch with a slidable magnet actuated by pulsing motion of the exerciser to provide electrical pulses to the calculator;

Figure 11:
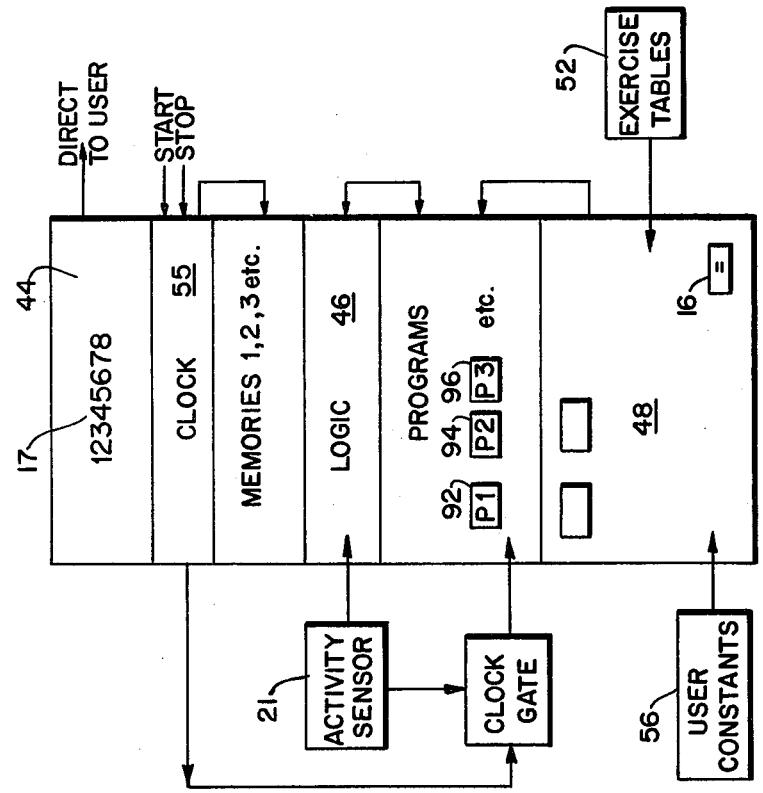
Figure 10:
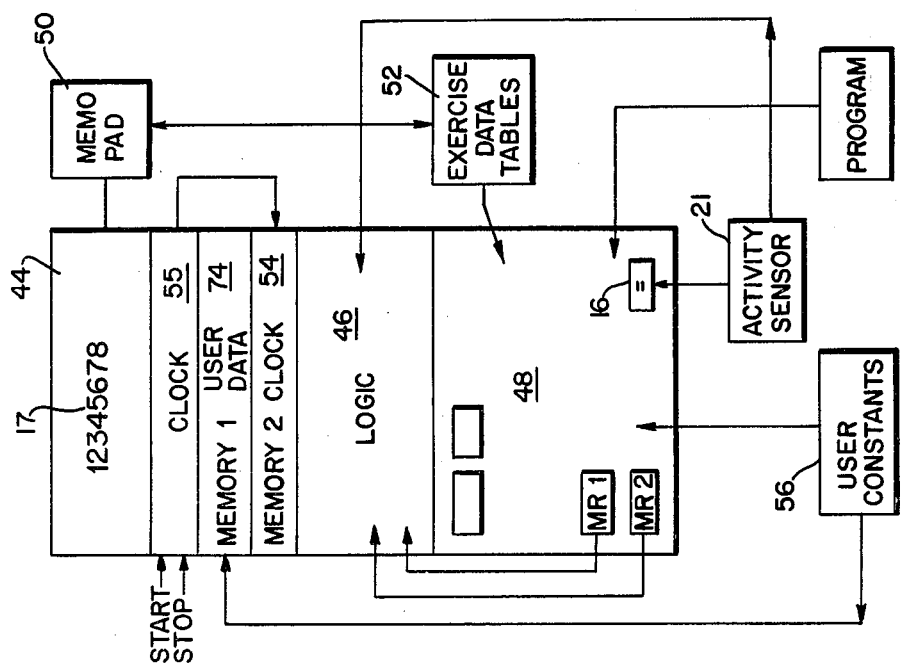

FIG. 10, more sophisticatedly, is a diagram including further means for measurement of energy output; and FIG. 11 is a diagram indicating use of a computer which is programmable combined with mechanism in which any form of exercise may be so programmed as to readily read the energy output in time, distance or calories.

Referring first to FIG. 1, a simple commercial computer 10 is shown digitally operated by a series of numbered keys 12 with mathematical modifying circuitry controlled by input keys 14 directing mathematical treatments, multiplication, subtraction, division or the like, including decimal modifications or other numbered mathematical treatment. It typically has an equals (=) transfer button 16. The numerical tally resulting from operation of this calculator is displayed in a row of eight digits at 17. If the computer is set with the display 1.000000, each movement of transfer button 16 will increase the last digit serially. Thus the calculator so set will serially count each pulse applied to the button 16. That button 16 has a lever 18 having its upper end disposed for pressing thereon, as shown in FIG. 1. The center of the lever 18 is mounted on a pivot 19. The lower end of the lever 20 is bent into a loop and contacts a transfer lever 22. The outer end of lever 22 is held in a pivot 24. The inner end of lever 22 is weighted downward by a weight 26 so that the center of lever 22 bears downward upon the loop 20. In that construction, movement of the total combination of the pocket-sized computer 10 by being carried by an exerciser in exercising motion, such as walking, jogging, or other muscular activity, will actuate the weight 26 and lever 22 against loop 20 for pivotal movement of lever 22 up and down in the direction of the arrow 28 with lever 18 moving resiliently on its pivot 19 to move the connecting arm 18 against the equals (=) button 16, transferring thereto a pressure pulse for each bob of the weight 26. This is a direct mechanical pulse transfer to the button 16, in turn connected to the mathematical circuit (not shown) of the computer 10. In alternate construction, the lever 18 may be disposed adjacent to a contact 54 connected to the output button 16 in turn connected to lead wires 66, as shown in FIG. 5, whereby depression of the lever 18 to contact the button 16 will close a circuit and supply an electrical pulse to the computer measuring each impulse movement of the weighted lever 22 upon the connecting arm electrically.

In a preferred form of use of the simple computer of FIG. 1, the pocket computer is disposed within a carrying case 32 which has a securing flap 38 and is bent over to form a loop 36 by which the case may be fastened to the belt of the exerciser. The computer can be inserted into the carrying case 32 and firmly secured therein by the flap 38 having fibrous fastening elements which securely fasten the computer therein, there being sufficient space at the bottom in which to house the weight 26, lever 22 and connecting arm 18. A lower panel wall 40 forms a shelf for supporting the computer above the bottom 42 of the carrying case. The lower panel 40 supports the computer above the bottom of the carrying case 42 which has sufficient space to allow free vibratory movement of the lever arm 22 and weight 26 at the lower end of the carrying case. In this assembled "plug-in" computer in a carrying case 32 the connecting arm is sized to rest against the button 16 of the computer 16 without pressure.

Figure 8:
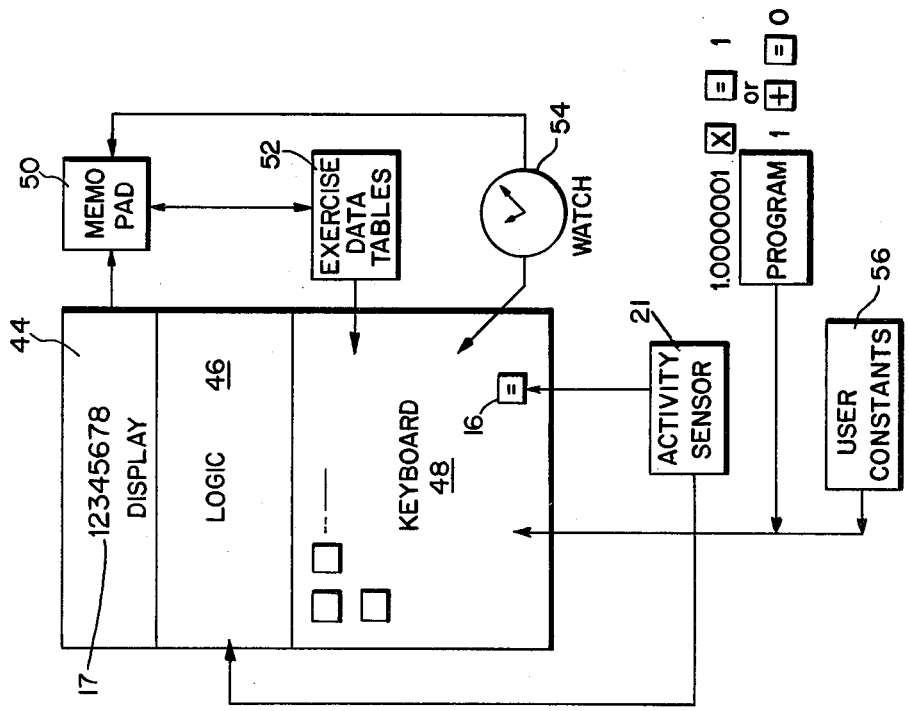
FIG. 8 shows a diagram of the useful elements including operations of the user for simple exercise recording.

In that simple form the computer is operated, as shown in FIG. 8. It will have a display portion 44 for the row of digits 17, a logic section 46 and a keyboard 48 generally indicating a typical pocket computer. The exerciser may have a memo pad 50 and a book of exercising data 52 tabularly indicating calories by certain types of exercises and may refer to his own watch 54 for timing. As he exercises from jogging, each stride or pace performed by the exerciser in jogging will cause a swing of the weight 26 to press the equals (=) button 16 on the keyboard 48. With the display showing originally the value 1.0000001, actuation of key 16 will progressively count the pulses and, in effect, will cause a repeat of whatever instructions were programmed into the computer by pressure of the equals (=) button 16. In the simplest type of computer, if one pressed the digit 1 and filled the total output display with zeros to the final number, any further pulse or count would increase the final number by one.

Consequently, even an ordinary computer without a repeat function would operate to tally each muscular movement of the exerciser numerically in a sequence. Hence the display then will show a numerical count of the movement or exercising pulses, even in the ordinary computer. The user would mark this tally on his memo pad. That number, referring to exercise data tabs 52 could be modified, for example, to divide by the length of time indicated by a timepiece or watch or stop watch 54, as desired, so that the actual numerical pulse count of the computer will be modified by the user calculating his distance or time expended; or even referring to the exercise data tabs, the number of calories that may be expended by a person of his weight in taking so many strides, paces, jumps, jogs or the like can be computed. Obviously, the ordinary function of the computer may be enlisted to complete his calculations.

Moreover, and quite important for combining the computer with the pulse count, each pulse can be modified by a factor supplied as indicated at 56 to modify the actual count of the pulses in order to then estimate the amount of energy associated with each pulse. For instance, the factor will vary between an exerciser jogging, swimming or walking, etc. Obviously, in the case of a swimmer the device will be encased in a waterproof case wherein perhaps an arm or leather strap is fastened thereto (not shown) but still activated by the muscular movement of the encased computer and pulse transducer for indicating the pulse count modified to the effort of the exerciser. The constant will modify the actual count, by applying through the keyboard a necessary factor whereby the final output tally displayed will be a modified reading reflecting both the individual muscular pulses as well as the energy associated with each. In that manner the exerciser can determine over a selected time period the distance he has gone, or the amount of calories he has expended, or the like.

The assembled sensor 21, as shown in FIG. 1, is a weighted spring lever arm having the weight 26 disposed on the outer end to accelerate the degree of resilient swing of the arm 22 adjusted against the loop 20 to contact the button 16. A modified construction is shown in FIG. 4, also shown as disassembled elements of FIG. 6 wherein the mass 50 is a metal ball held within a box-like encasement 52 having a resilient spring arm bottom 58 biased to a contact point 54 with the inner end secured to one of the walls 62. Thus the bottom 58 is fastened by an arm 60 to an opposite wall 62 and forms the second contact point. The lower bottom arm 58 is resilient and pressed by the weighted wall 50 thereon and the total assembly moves with the muscular motion. The resilient arm 58 moves up and down in the direction of the arrow 64 with the motion of the exerciser to whom the device is fastened. In each stride or step, the resilient arm 58 will make contact with the arm 54 completing a circuit therethrough which is carried by wires 66 to complete the contact to key 16, as shown in FIG. 5. Thus instead of a weighted mass 26 carried on the weight of a lever, the weight may be a loose body 50 held in a container 52, which by muscular motion of the assembly depresses the arm 58 to make contact with the arm 50, completing the circuit by way of wires 66 back to the equals (=) key 16.

The entire assembled sensor 21, as shown in FIG. 5, may be mounted in the upper end 68 of a container 32 which may also house a battery 70 having contacts 72 which activate the calculator.

Figure 9:
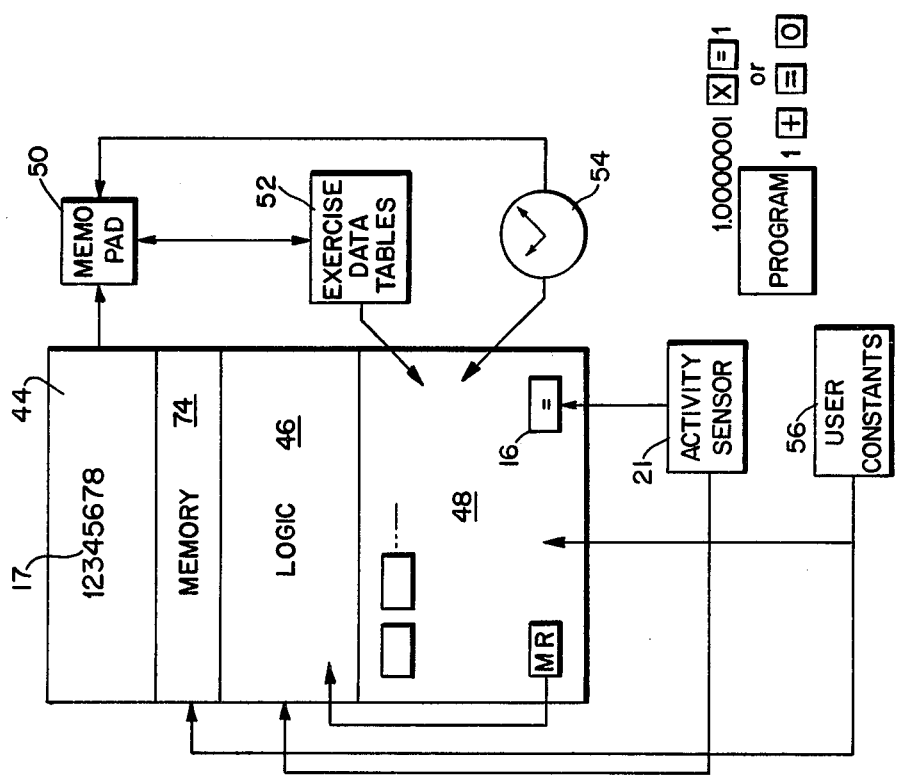
FIG. 9 is a slightly more sophisticated diagram which includes incorporation of memory repeated additions combined with a clock means for providing exercise data in timed measurement.

A similar diagram for operation of a slightly more sophisticated unit is shown in FIG. 9, which may differ from FIG. 8 by having a more sophisticated computer having a built-in memory unit, whereby each jog or muscular movement of the exerciser may be directly counted by being programmed for repeat, etc. by pressing a one plus button. That is, the computer is here used as a repeat function. With that type of more sophisticated computer, initial programming will repeat with the pressing of the equals (=) key 16 by a signal from the pulse or activity sensor 21. Thus, either as shown in FIGS. 8 or 9, a simple computer, or a more sophisticated computer having a repeat system therein, can be used.

As shown in FIG. 7, a unique reed type of switch is formed using a pair of opposed polarity magnets 76 and 78, the latter being mounted to slide in a guide groove carried by a confining rail 80 in a housing of non-magnetic material, both magnets being mounted to have the same opposed polarity, whereby they magnetically repel each other. The movable magnet 78 is normally slidably supported in the housing and repelled by the stationary magnet 76, will be held by the opposed polarity magnet at a variable distance 82 above magnet 76 mounted fixedly therebeneath, thus providing the separating space 82. As thus mounted for vertical sliding movement, as exercising movement of the assembled switch, the repelled movable magnet 78 will move upwardly and downwardly responsive to the mechanical movement of an exerciser with each stride, step, pace or analogous muscular movement. A dampener 81 is mounted above to reduce vibration of the magnet. Thus, in movement of the magnet 78 downwardly in the direction of the arrow 83, reducing the space between the magnets, against the repulsive magnetic force of magnet 76, the movement will be resilient because the magnetic repelling flux as the magnets move closer together will increase and become great enough in due course to offset the downward movement of movable magnet 78, thus moving the magnet 76 upward. This will cause a pattern of variation in the magnetic field therebetween with each mechanical pulse in which the magnets slidingly oscillate towards and away from each other. The guide for the sliding magnet may be lubricated. A reed switch 84 is mounted opposite the open space 82 of the oscillating magnet. The switch 84 comprises a pair of stiff magnetic metal contacts, such as resilient steel wires 86, mounted close together, but normally out of conductive contact with each other. The wires are supported in a space 88, the upper wire contacting an outlet current lead 90 and the lower contacting lead 89. The wires 86 mounted close to space 82, are magnetically responsive so that when the magnetic flux built up by the descending magnet 78 is great enough, quite strong relative to the steel wires, and strong enough to attract the resilient wires 86, these will be bent by the magnetic attraction into electroconductive contact with each other. Since the wires are resilient, as the magnet 78 bounces upward in its oscillating movement by the replusion of the magnetic field, the reduction of magnetic flux between the wires 86 will be sufficiently resilient to separate them, thus alternately making and breaking of the circuit between the wires 86 and between leads 89 and 90. Thus by slidably bouncing of opposed polarity magnet 78 as opposed by magnet 76 responsive to the mechanical motion of the exerciser or the like to which the total switch is attached, the circuit between wires 86 and lead wires 89 and 90 will be made and broken alternately with the mechanical pulsing force to which the assembly is subjected by the exerciser. Lead wires 89 and 90 are connected to complete the circuit through the equals (=) key 16 as before, whereby this switch may be alternately substituted for other impulse or activity sensors 21.

This magnetic type of switch as described operative by simple mechanical motion of a moving body, is preferably used as a pulse counter in any kind of circuit such as a computer to tally the pulses, or a computer to modify the tallied number of pulses to other useful data. However, this switch may have broader uses than in an exercising device. It can be used to measure any motion, such as to count reciprocations or oscillating motions of a pendulum, spring or the like, by mounting the switch relative to the motion of the moving body by which motion is to be measured connecting it in a manner such that the magnet of opposed polarity will move slidingly with the oscillating motion being measured and to count the electrical pulses.

However, there is particular advantage in the reed switch structure herein shown in combination with the computer since it may also be mounted a distance remote from the computer and connection thereto either by an electrical lead wire, or it may be connected to radio circuitry to broadcast the electrical pulses produced by the mechanical motion of the sliding magnet 78. For this purpose it is possible to mount such sensor to the body of each exerciser or a substantial group of persons to measure their activity by a computer with signals from each carried by lead wires or radio broadcast signals which can be handled by a multiple entry computer both of large fixed installation type or by a portable type of computer of more sophistication, whereby the movement of each member of an exercising group can be tallied. Such broadcast signals may be taken as leads 67 from output lead wires 66 and broadcast as signals from a conventional radio broadcast means 69, as shown diagrammatically in FIG. 4, in which element 69 refers to such radio signalling means. In this manner the exercise or work output of an assembled group of workers or exercisers drilling as a team or playing as a team can be measured as an individual in any useful form of data or as a composite output, as desired.

A somewhat more sophisticated assembly of elements, as shown in FIGS. 10 and 11, may be used. For instance, as shown in FIG. 10, a computer having memory usefully programmed therein indicated by 74, may also have a timing mechanism or watch 54 combined with the computer and this may be a visibly indicating timepiece, or it can operate as a stop watch connected to the memory of the computer for programming a selected time period of exercise. A visibly mounted watch 55 can be used in the combination and this will be combined with stop and start means, typically a stop watch connected to the memory 54, started when the exercise begins and the program timing may automatically terminate at a preselected time period. The program for such intermediate type computer beyond timing can be further modified for a particular number of pulses in exercising. It can be modified for the type of exercise or for mathematical conversion by the computer to a corresponding calorie output by introducing into the computer a factor significant of each exercise motion. Thus, the readout or display 44 of the device shown in FIG. 10 can have a considerable degree of sophistication, but again much of it will be programmed into the relatively simple computer, even though it may be a repeat type computer, by programming it with data inserted by the user himself to obtain the kind of display readout that interests him the most; that is, the readout can be in paces per hour; it could be the total calorie output of the exerciser, or modified by a timing mechanism whereby the exercising is measured over the selected period.

A further degree of sophistication can be in the device shown in FIG. 11 where the computer itself is so sophisticated as to include programming with several kinds of programs controlled by memory input switches 92, 94, 96, etc., for activating a program of a distinct type, whereby the computer will then operate responsive to the predetermined routine or data sequence. Thus one modifying program may differ from another by the type of exercising, jogging, swimming, cycling, walking or the like, each having its own program. Again, each may have a different time sequence or different calorie or pace factor, whereby the readout for the program will be followed for the type of exercise as selected by the user, and it may be modified also by timing data, or the like.

It will be appreciated, therefore, that the computer hereof can be simple, or progressively sophisticated, whereby the user will use the computer to do his own computations or tally, or the computer may be programmed to readout any desired information. For instance, he will determine the average of his own pace or stride, as a measured distance, and will convert the tallied number of strides over a preselected distance as in walking or jogging a selected distance, to determine the average length of his stride; or will modify the total to a calorie output as an overall measurement of the modified exercise; or may modify total comptation further in terms of a time or a rate of motion. Thus, he can use the calculator to obtain therefrom any further data in which he is interested, based upon the original tally of the pulses imparted to the calculator by the counting or tallying of each pulse. The same result can be obtained automatically without need for a personal computation by having preprogrammed into a type of computer in which a further timing mechanism will be employed to obtain a readout of this type of data selectively, depending upon the kind of exercise programmed, as he wishes.

In preferred construction, the computer is a small pocket-sized device which he can carry upon his person, typically in a pocket or strapped to his belt, wrist, or leg, particularly the portion of his body which will most significantly supply the pulse output, variable with the selected exercise. The invention may be made useful more broadly by using a sensor transducer having a radio output to broadcast pulses which can be received by a stationary and even larger computer disposed a significant distance from the exerciser, whereby a number of exercising persons each carrying a pulse transducer can broadcast the pulses to one or more receivers a substantial distance away, and in which the receiver is a calculator or computer capable as described of tallying the pulses directly or in calculated or computed modified form.

A preferred form of pulse transducer as described above is a magnetically sensitized reed switch to sense mechanical motion of a slidable magnet.

Other uses of the device hereof will occur to those skilled in the art, and accordingly, the description herein is to be regarded as exemplary and not limiting except as defined in the claims.

I claim:

1. The portable exercise measuring device, comprising, in combination, a mechanical sensor-transducer, having outputs representative of muscular movements of an exercising body, said transducer comprising a movable inertial mass; a computer for converting said output to signals representative of the number of Calories expended by said exercising body, said computer including means for accumulating the total number of said signals and displaying said total; and timing means connected to said computer for modifying the sum of said accumulation dependent upon the type, vigor or period of the exercise.

2. The combination as defined in claim 1 wherein the computer is a mini-computer having electrical contact input means connected in circuit with the inertial mass sensor activated by said exercising muscular movements to modify the periods of said timer, said measuring device being enclosed in a pocket carrying case mountable to the body of the exerciser.

3. The combination as defined in claim 1, wherein said outputs of said sensor transducer are connected to the input of said computer as mechanical pulse signals.

4. The conmbination as defined in claim 1 wherein said outputs of said sensor transducer are converted to electrical signals and directly transferred to said computer through electro conductive wiring inter-connecting said transducer and said computer.

5. The combination as defined in claim 4 wherein said outputs of said sensor transducer are converted to electrical signals, said transducer is further combined with radio transmitting means, whereby said signals are radio broadcast, and said computer is combined with radio receiving means tuned to receive said signals and transfer the received signals to the memory of said computer.

6. The combination as defined in claim 1, wherein the transducer is a pivotally supported arm and the inertial mass is a weight secured near an end thereof, whereby mechanical motion will cause the weighted lever to swing on its pivot in an arc and transferring its movement to an input key of said computer to signal the mechanical pulse generated by each pivotal movement of said lever.

7. The combination as defined in claim 6, wherein said lever carries an electrical contact means to close a circuit periodically with each movement thereof, said circuit connected to the input of said computer to count said movements.

8. The combination as defined in claim 1, wherein said transducer comprises a weight supported on a resilient arm above an electrical contact means electrically connected to the computer, said weight being confined in a housing above said lever and movable in response to mechanical exercising motions imparted to said combined elements, each motion imparting a momentum to said weight sufficient to depress said lever upon said electrical contact to supply an electrical output countable by said computer.

9. The combination as defined in claim 1, wherein said transducer comprises a reed switch comprising a pair of magnetically responsive resilient metal wires separately supported close to bend under magnetic influence out of electrical contact with each other, each having an electrical lead secured thereto for conveying current completed through said wires on contact with each other, a pair of magnets supported in a framework, each with a polarity positioned opposed to the other, one magnet being fixed in said framework and the other mounted slidably therein to be pressed away from the other magnetically a significant distance by the opposed flux, the assembly of magnets being disposed sufficiently close and having a strong enough combined flux in closest position one to the other to depress said switching wires into electroconductive contact with each other, whereby the slidable magnet responsive to mechanical motion of the assembly will slide closer and then away from the fixed magnet, oscillatingly, first to magnetically attract said wires closing their contact with increased flux as the magnets are close to each other, and then release said wires, breaking their contact when the movable magnet slides away to decrease the magnetic flux with said mechanical motion.

10. The combination of claim 1, wherein the computer or calculator has a repeat function and the transducer is connected to actuate to said repeat function with each transduced pulse of said transducer.

11. The combination as defined in claim 1, wherein the timing means includes a plurality of timing means for measuring the period of exercising, the Calories expended and the rate of exercising.

12. The combination as defined in claim 1, wherein the computer has a means for programming to modify the accumulated tally according to the type of exercise performed.

13. The portable exercise measuring device, comprising, in combination, a mechanical sensor-transducer, having outputs representative of muscular movements of an exercising body, said transducer comprising a movable inertial mass; a computer for converting said output to signals representative of the number of Calories expended by said exercising body, said computer including means for accumulating the total number of said signals and displaying said total; and timing means connected to said computer for modifying the sum of said accumulation dependant upon the type, vigor or period of the exercise, said computer and transducer being pocket-sized and both are mounted in a carrying case portably supported by the exercising user in his pocket or belt, said carrying case permanently having mounted therein the sensor-transducer to mechanically connect to the removable computer to transfer the sensed mechanical exercising signals to the inserted computer.

14. The combination as defined in claim 13, wherein the transducer is mounted in position to transfer the transduced exercising pulses to an input of said calculator, whereby the assembled mounting of said computer in said carrying case provides a plugged-in contact between said transducer and to input of said computer.

* * * * *